(12) United States Patent
Stedman et al.

(10) Patent No.: US 6,701,256 B2
(45) Date of Patent: Mar. 2, 2004

(54) EXHAUST OPACITY MEASURING DEVICE

(75) Inventors: Donald H. Stedman, Denver, CO (US); Gary A. Bishop, Louisville, CO (US); Gary Full, Tucson, AZ (US)

(73) Assignee: Environmental Systems Products Holdings Inc., East Granby, CT (US)

( * ) Notice: Subject to any disclaimer, the term of this patent is extended or adjusted under 35 U.S.C. 154(b) by 0 days.

(21) Appl. No.: 10/093,714

(22) Filed: Mar. 11, 2002

(65) Prior Publication Data

US 2003/0225532 A1 Dec. 4, 2003

Related U.S. Application Data

(60) Provisional application No. 60/318,574, filed on Sep. 11, 2001.

(51) Int. Cl.[7] .............................................. G01N 31/00
(52) U.S. Cl. ........................................ 702/24; 73/23.36
(58) Field of Search .............................. 702/24, 31, 32, 702/66, 71; 73/23.2, 23.22, 23.35, 23.36, 23.37; 340/632–634, 815.55, 815.57; 324/122

(56) References Cited

U.S. PATENT DOCUMENTS

| | | | | |
|---|---|---|---|---|
| 3,768,908 A | * | 10/1973 | Zaromb | 356/338 |
| 3,989,938 A | * | 11/1976 | Auth | 702/24 |
| 4,467,435 A | * | 8/1984 | Warnke et al. | 702/24 |
| 4,801,209 A | * | 1/1989 | Wadlow | 356/417 |
| 5,210,702 A | * | 5/1993 | Bishop et al. | 702/24 |
| 5,351,198 A | * | 9/1994 | Adachi et al. | 702/24 |
| 5,831,267 A | * | 11/1998 | Jack et al. | 250/338.5 |
| 5,884,226 A | * | 3/1999 | Anderson et al. | 702/3 |
| 6,025,920 A | * | 2/2000 | Dec | 356/438 |
| 6,286,360 B1 | * | 9/2001 | Drzewiecki | 73/24.01 |

OTHER PUBLICATIONS

Stedman, Donald, "On–Road CO, HC, NO and Opacity Measurements", 7th *CRC On–Road Vehicle Emissions Workshop*, Apr. 9–11, 1997, pp. 8–25 and 8–27 to 8–33.

* cited by examiner

*Primary Examiner*—Marc S. Hoff
*Assistant Examiner*—Mary Catherine Baran
(74) *Attorney, Agent, or Firm*—Mintz Levin Ferris Glovsky and Popeo PC (57) ABSTRACT

A remote emissions sensing system and method for sensing exhaust emissions from motor vehicles is provided where the system determines the opacity of an exhaust plume. The system comprises a radiation source that emits radiation which is passed through the exhaust plume of a motor vehicle to one or more detectors arranged to receive the radiation. Multiple wavelength opacity measuring embodiments and monochromatic wavelength opacity measuring embodiments are disclosed.

8 Claims, 9 Drawing Sheets

EXHAUST OPACITY MEASURING DEVICE

RELATED APPLICATIONS

This application claims priority to U.S. Provisional Patent Application Serial No. 60/318,574, filed Sep. 11, 2001 and titled "System and Method For Detecting Smoke Density In Exhaust Emissions."

FIELD OF THE INVENTION

The present invention relates to a remote emissions sensing system and method for sensing exhaust emissions from motor vehicles where the system determines the opacity of an exhaust plume.

BACKGROUND OF THE INVENTION

Remote emission sensing (RES) systems are known. One such system is disclosed in U.S. Pat. No. 5,210,702 and comprises an electromagnetic (EM) radiation source that is arranged to pass a beam of EM radiation through the exhaust plume of a motor vehicle as the motor vehicle passes by the system. The system also comprises one or more detectors arranged to receive the radiation after it passes through the exhaust plume of the vehicle. One or more filters may be associated with the one or more detectors to enable the detectors to determine the intensity of EM radiation having a particular wavelength or range of wavelengths. The wavelengths may be conveniently selected to correspond to wavelengths absorbed by molecular species of interest in an exhaust plume (e.g., hydrocarbons (HC), carbon monoxide (CO), carbon dioxide ($CO_2$) and nitrogen oxides ($NO_x$) such as NO and $NO_2$. The one or more detector output voltages represent the intensity of the EM radiation measured by that detector.

These voltages are then input to a processor. The processor calculates the difference between the known intensity of the light source and the intensity detected by the detectors to determine the amount of absorption by the particular molecular species (based on predetermined wavelengths associated with that species). Based on the measured absorption(s), the concentration of one or more molecular species in the emissions may be determined in a known manner.

A system for the remote sensing of exhaust opacity is disclosed in "Feasibility of Remote Sensing of Particulate Emissions From Heavy-Duty Vehicles," Chen, G. et al., American Society of Automotive Engineers (1996). In this system, opacity is measured at a wavelength of 638 nm and correlated with $CO_2$ measurements.

Existing RES systems suffer from various drawbacks and limitations. These factors may lead to erroneous readings, a relatively high incidence of discarded data or a relatively high incidence of "flagged" test results. These and other problems can reduce the benefits of an RES system.

At least some RES systems work, in part, by determining the absorption (or transmittance) of light through an exhaust plume. By determining the absorption/transmittance at particular wavelengths (corresponding to wavelengths at which various molecular species present in an exhaust plume absorb EM radiation), the concentration of those species in the exhaust can be determined. One problem is that various outside factors may affect the measured intensity and lead to errors. For example, if the measured intensity is reduced due to light scattering by particles in the exhaust plume, rather than absorption of the radiation by the species of interest, this can lead to errors.

One drawback of some remote sensing systems is the use of a single wavelength of EM radiation to measure opacity. It is known that EM radiation scattering due to the presence of particles increases with decreasing wavelength. Because scattering is a major contributor to a plume's opacity, systems that measure opacity with only relatively long wavelength EM radiation may often yield inaccurate results.

These and other drawbacks exist.

SUMMARY OF THE INVENTION

One advantage of the invention is that it overcomes these and other drawbacks in existing devices.

Another advantage of the present invention is to provide a remote emissions sensing system and method that is capable of remotely monitoring the opacity of exhaust from vehicles.

Another advantage of the invention is to improve the accuracy of remote emissions sensing systems and methods by measuring exhaust opacity and utilizing that measured exhaust opacity to ensure the accuracy of other measurements.

Another advantage of the invention is to provide existing emission monitoring equipment with exhaust opacity monitoring capability.

These and other objects of the invention are accomplished according to various embodiments of the present invention. According to one embodiment, a RES system and method comprises a radiation source that is arranged to pass a beam of radiation through the exhaust plume of a motor vehicle as the motor vehicle passes by the system. One or more detectors are arranged to receive the radiation after it passes through the exhaust plume of the vehicle.

The one or more detectors output a voltage corresponding to the intensity of the radiation received by that detector. These voltages are then input to a processor. The processor calculates the difference between the known intensity of the light source and the intensity detected by the detectors to determine the amount of absorption by the particular molecular species (based on predetermined wavelengths associated with that species). Based on the measured absorption(s), the concentration of one or more molecular species in the emissions may be determined.

According to one aspect of the invention, the output of a reference detector is supplied to a processor and monitored by the processor to determine the opacity of each exhaust plume. Based on the measured opacity, a predetermined action may be taken. For example, if the exhaust opacity exceeds a predetermined level, the emissions data may be analyzed to produce test results (in a known manner), but the test results may be "flagged" as suspect or discarded.

According to another embodiment of the invention, a system and method for measuring opacity comprises multiple sources of EM radiation having diverse wavelengths and the appropriate detector or detectors to detect the diverse wavelengths. The multiple sources of EM radiation are arranged to enable a beam (or beams) of EM radiation to pass through an exhaust emission plume. Signals from the detector (or detectors) are processed to determine, among other things, the change in intensity (e.g., intensity without emission plume present versus intensity with emission plume present) for each of the wavelengths. The change in intensity is correlated to the relative concentration of at least one emission plume constituent (e.g., carbon dioxide ($CO_2$)). Change in intensity measurements that correlate to a sufficient degree (e.g., a regression with a standard error of the slope less than 20% of the slope value) are registered as valid opacity values.

Another embodiment of the invention enables calculation of a smoke density value that is proportional to the opacity of the plume. This embodiment may comprise a substantially monochromatic EM radiation source (e.g., a laser, or other monochromatic source) that directs EM radiation through a volume of an emission plume. Appropriate detectors obtain a measurement of the transmittance (T) of the beam through the plume. A measurement of an amount of an exhaust constituent (e.g., $CO_2$) is performed for substantially the same volume of the emission plume. The calculation of the smoke density value for the plume is made using the measured transmittance value (T) and the measured amount of exhaust constituent.

Other objects and advantages of the present invention will be apparent to one of ordinary skill in the art upon reviewing the description herein.

DETAILED DESCRIPTION OF THE DRAWINGS

Figure 1:
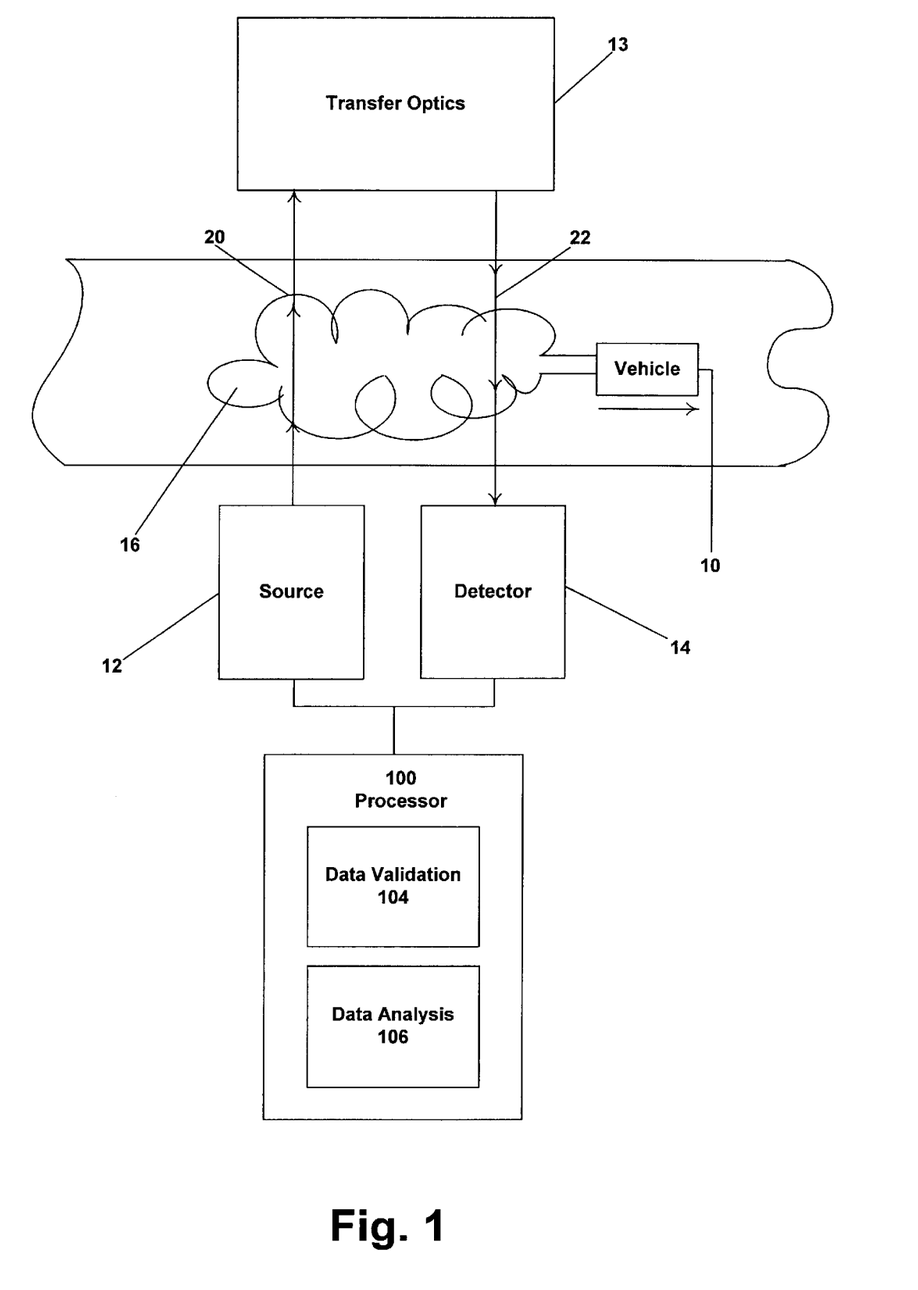
FIG. 1 depicts a remote emissions sensing device (RES) according to one embodiment of the present invention.

FIG. 1 depicts an RES according to one embodiment of the present invention. The RES measures emissions from a vehicle 10. The RES comprises a source 12 for generating radiation 20. Radiation 20 is directed through the exhaust plume 16 of a vehicle 10 as vehicle 10 passes by the RES. Transfer optics 18 receive the radiation 20 and transfer the radiation 20 through plume 16 as post-plume radiation 22 to one or more detectors 14. Detectors 14 are arranged to measure said radiation 22 after it passes through exhaust plume 16 of vehicle 10. A filter (not shown) may be associated with one or more detectors 14 to enable detector 14 to determine the intensity of radiation having a particular wavelength or range of wavelengths by filtering out all but the particular wavelength or range of wavelengths from return radiation 22. Alternatively, tuned lasers can be employed as source 12 to generate radiation 20 of a particular wavelength or range of wavelengths, in which case filters may not be required.

The wavelengths may be conveniently selected to correspond to wavelengths absorbed by molecular species of interest in an exhaust plume (e.g., HC, CO, $CO_2$, NO, $NO_2$ (hereinafter $NO_x$), or other molecular species). One or more detector output voltages representing the intensity of the radiation 22 measured by that detector 14 are obtained. The detector output voltages are input into a processor 100. Detector 14 may be any suitable detector such as a photodiode, photomultiplier, charge-coupled detector, indium antimonide, lead selenide, or other known photoconductive or photovoltaic detectors.

Preferably, the source 12 is maintained at a substantially constant temperature by, for example, enclosing source 12 in a housing to insulate it from atmospheric conditions such as sun, wind and rain. Temperature variations at source 12 may introduce additional error in the measurements.

Processor 100 may calculate the difference between the original intensity of the radiation 20 and the intensity of the radiation 22 detected by detector 14 to determine the amount of radiation absorption by particular molecular species at predetermined wavelengths associated with that species. Based on the measured absorption(s), the concentration of one or more molecular species in the emissions may be determined in a known manner. Such systems generally take a plurality of measurements (e.g., 50) over a predetermined period of time (e.g., 0.5 seconds). These data points are then correlated and analyzed to determine concentrations of target emissions species.

According to one embodiment of the present invention, processor 100 may perform various functions including determining concentrations of various emission components. As discussed above, the device of FIG. 1 monitors several channels, each for a separate emission component.

According to one embodiment of the present invention, the RES may be used for diesel vehicles, and particularly heavy-duty diesel vehicles such as trucks and buses. The present invention may be used to measure the concentration of various emission components as well as the amount of particulate emissions in the exhaust of a diesel vehicle. Gaseous and particulate emissions together contribute a substantial amount of pollutants to the environment. In particular, heavy-duty diesel vehicles produce a substantial amount of $NO_x$ as well as particulate emissions. Due to the probable carcinogenic nature of diesel particulate emissions, stringent regulations are generally imposed on such emissions.

Exhaust opacity is a measurement of the particulate emissions from a vehicle.

In measuring the opacity of vehicle emissions, an opacity measurement, a CO measurement and a $CO_2$ measurement may be taken to obtain a reliable and accurate measure of opacity. Any measurement of opacity inherently contains a certain error factor which results from the dilution of the exhaust plume with ambient air. A corresponding measurement of $CO_2$ concentration taken at the same time as the opacity measurement will reflect the same dilution of the exhaust plume by ambient air. Based upon a predetermined expectation of the level of $CO_2$ in an exhaust plume, and taking a ratio of the opacity measurement and a $CO_2$ measurement, the dilution factor is compensated thereby resulting in an accurate measurement of fuel specific opacity.

The opacity measurement may be further verified in the case of diesel powered vehicles by comparing it to a CO measurement taken from the same exhaust plume at substantially the same time. The amount of CO in the plume is generally correlated to the amount of opacity of the plume. Therefore, if the amount of opacity is high, the amount of CO should also be high. If the amount of CO is low, while the amount of opacity is measured to be high, this may serve as an indication of a possible error in the opacity measurement or possible interference with the measurement due to other factors.

In a more preferred embodiment, a separate opacity channel is employed to determine opacity. The separate channel preferably uses radiation of wavelengths of about 0.20–1.50 microns. This wavelength range is expected to provide more accurate opacity measurements. Such a system may also include at least a $CO_2$, CO and reference channel.

Figure 2:
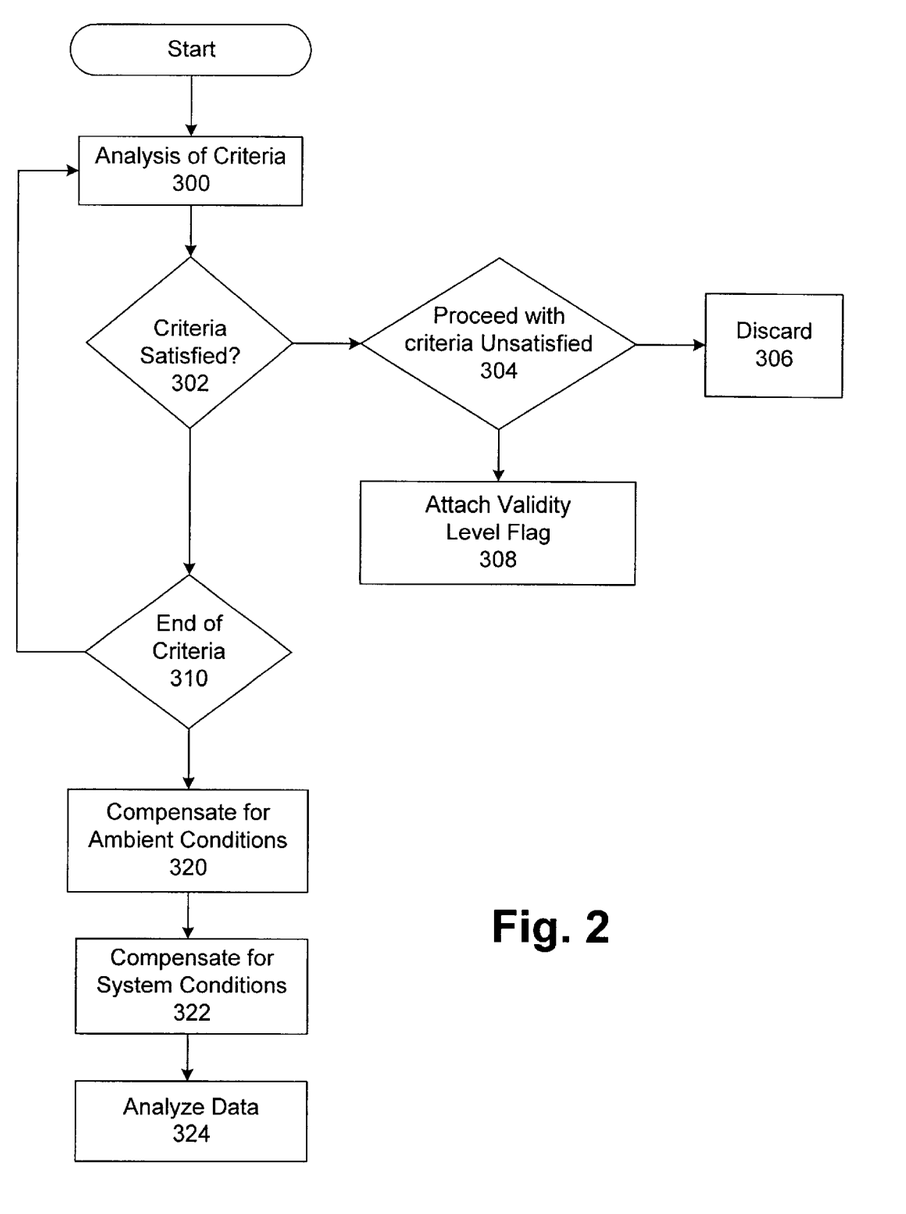
FIG. 2 depicts a data analysis method according to one embodiment of the present invention.

According to one embodiment of the present invention, a method for analyzing emissions may be described with reference to FIG. 2. In step 300, certain criteria are provided. The criteria used to analyze the measurement may vary depending on the particular emission concerned. In step 302, if the criteria are satisfied, then in step 310, the process proceeds back to step 300 to determine if more criteria are left to be analyzed. That process continues until, in step 310, there are no more criteria to analyze.

In step 302, if the criteria are not satisfied, then the process determines in step 304 whether the criteria are unsatisfied to a point where they are to be discarded in step 306 or whether they are to be simply flagged in step 308.

After criteria have been satisfied, in step 320, the results may be compensated for ambient conditions. In step 322, the system compensates for system conditions and in step 324, the data may further be analyzed. This overall method will be better understood with reference to the following embodiment of the present invention.

Figure 3:
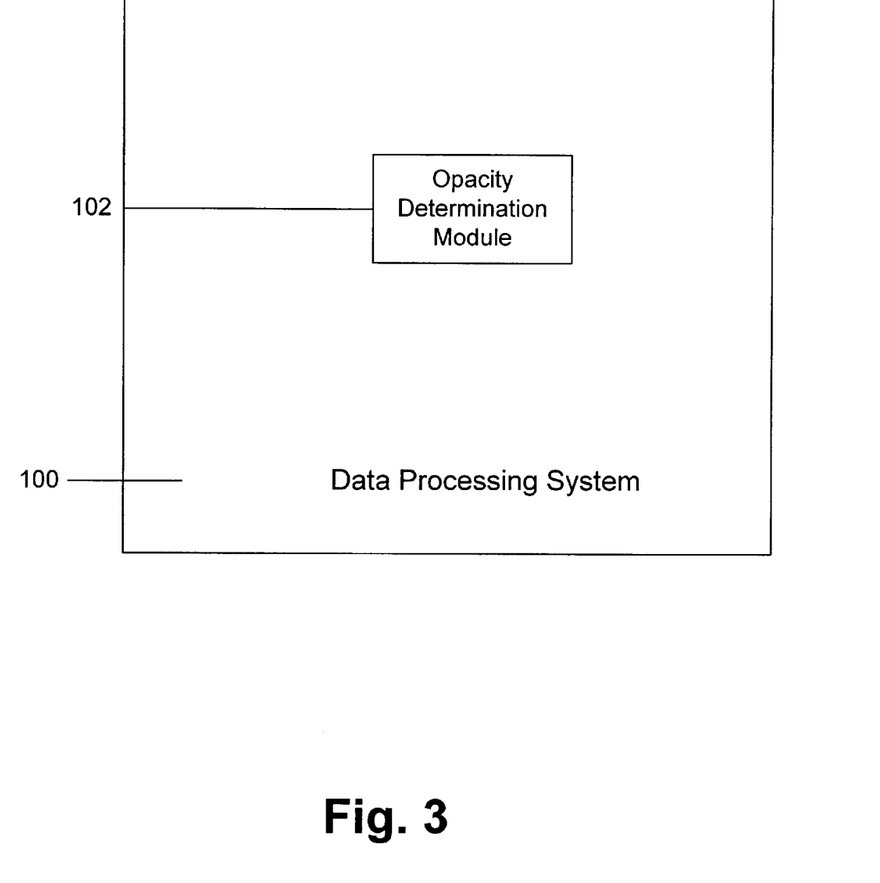
FIG. 3 depicts a processing system according to one embodiment of the present invention.

According to one embodiment of the present invention, the criteria may comprise opacity validation. According to this embodiment, the outputs of the one or more detectors of the RES system are input to processor 100 as depicted in FIG. 3. Processor 100 may comprise an exhaust opacity determination unit 102. Processor 100 may perform various known functions including determining concentrations of various gaseous emissions. Additionally, processor 100 may also determine exhaust opacity from the measurements taken, through exhaust opacity determination unit 102.

According to one embodiment, exhaust opacity determination unit 102 may determine exhaust opacity using the reference channel of the RES system by taking measurements of opacity at a wavelength of about 3.9 μm. Exhaust opacity determination unit 102 receives measurements from the reference channel and at least one other channel of interest. According to one embodiment, the channel of interest may be the $CO_2$ channel.

For each particular time interval measured, if the intensity of the reference channel is less than the input intensity of the radiation 20 normally generated by the radiation source 12, then processor 100 compares the reference channel intensity attenuation with that on the $CO_2$ channel. If the detected intensity of the reference channel drops, it is determined that particles in the exhaust plume are blocking or deflecting a portion of the radiation 20 which then does not return to the detector 14 as post-plume radiation 22. Opacity results from radiation scattering and absorption by the particulate matter present in the exhaust plume.

According to one embodiment of the present invention, the output of one or more of the detectors may be used in determining the opacity of the exhaust plume emanating from a vehicle being tested. The output of the detector (voltage level) may be monitored by processor 100. A voltage drop in the reference channel may be used to indicate and determine opacity of the exhaust. Accordingly, the wavelength or wavelength band detected by the reference channel may be specifically selected so that components of the emission, including $CO_2$, CO, HC, and $NO_x$, do not interfere with the opacity readings.

The determination of opacity in an exhaust plume may include the exhaust from heavy-duty diesel vehicles where the exhaust may comprise particles, such as dry soot. Generally, most diesel particles may range from 0.02–0.5 microns in size. According to the present invention, the output of one or more detectors may be used to calculate the opacity of the exhaust plume of a heavy-duty diesel vehicle being tested. The output of the detector may be monitored by processor 100 for changes in radiation intensity due to particles, such as soot, of the diesel exhaust plume. The degree of change in radiation intensity detected may then be used to measure the opacity of the diesel exhaust emission.

Measured reductions in the reference channel intensity may be used to correct gas measurement wavelengths for ambient noise, opacity and other factors because pollutant gases do not absorb at the reference wavelength. The measured pollutant wavelength absorptions may then be converted to apparent concentration values. If at least one of the apparent concentration values exceed a predetermined minimum, the pollutant concentrations may be correlated with the measured $CO_2$. The slopes are the ratios of the measured pollutants to the measured $CO_2$. These slopes can be used to carry out other calculations as described elsewhere herein.

In a more preferred embodiment, the opacity measurement is employed to validate measurements of the other components in the exhaust plume. A high opacity value indicates the presence of a large amount of particulate matter in the exhaust plume which may result in the scattering or absorption of radiation at one or more of the characteristic wavelengths for various components of the exhaust plume. This may cause inaccurate readings for these various components.

In such a case, the RES may label readings taken when a high opacity is present as suspect or invalid. More preferably, these readings are labeled invalid and additional readings are taken after a time delay. To implement this, the RES can monitor opacity and/or CO readings until opacity and/or CO concentration fall below a predetermined level deemed to be acceptable for taking readings for various exhaust components such as CO, $CO_2$, HC, NO and $NO_2$. The presence of sufficient plume for the measurements after the time delay can be verified using the $CO_2$ reading. In this manner, the RES may provide accurate measurements of exhaust components even when the initial exhaust plume has a high opacity that would normally introduce a significant error into such measurements.

Percent opacity is subject to rapid attenuation by various factors, such as air, wind, and turbulence behind the vehicle. Since $CO_2$ readings can be used as a tracer of where the exhaust plume is seen, if the correlation to $CO_2$ is not accurate (i.e., there is a large error in the slope), then the opacity measurement may be presumed as from being from another source, such as dirt from tires, and the reading is rejected. If the correlation is accurate (i.e., there is a small error in the slope), then multiplication of the measured slope by a correction factor, such as 1000, depending on the calibrations and the units of measurement used, leads to a standardized opacity.

Figure 4:
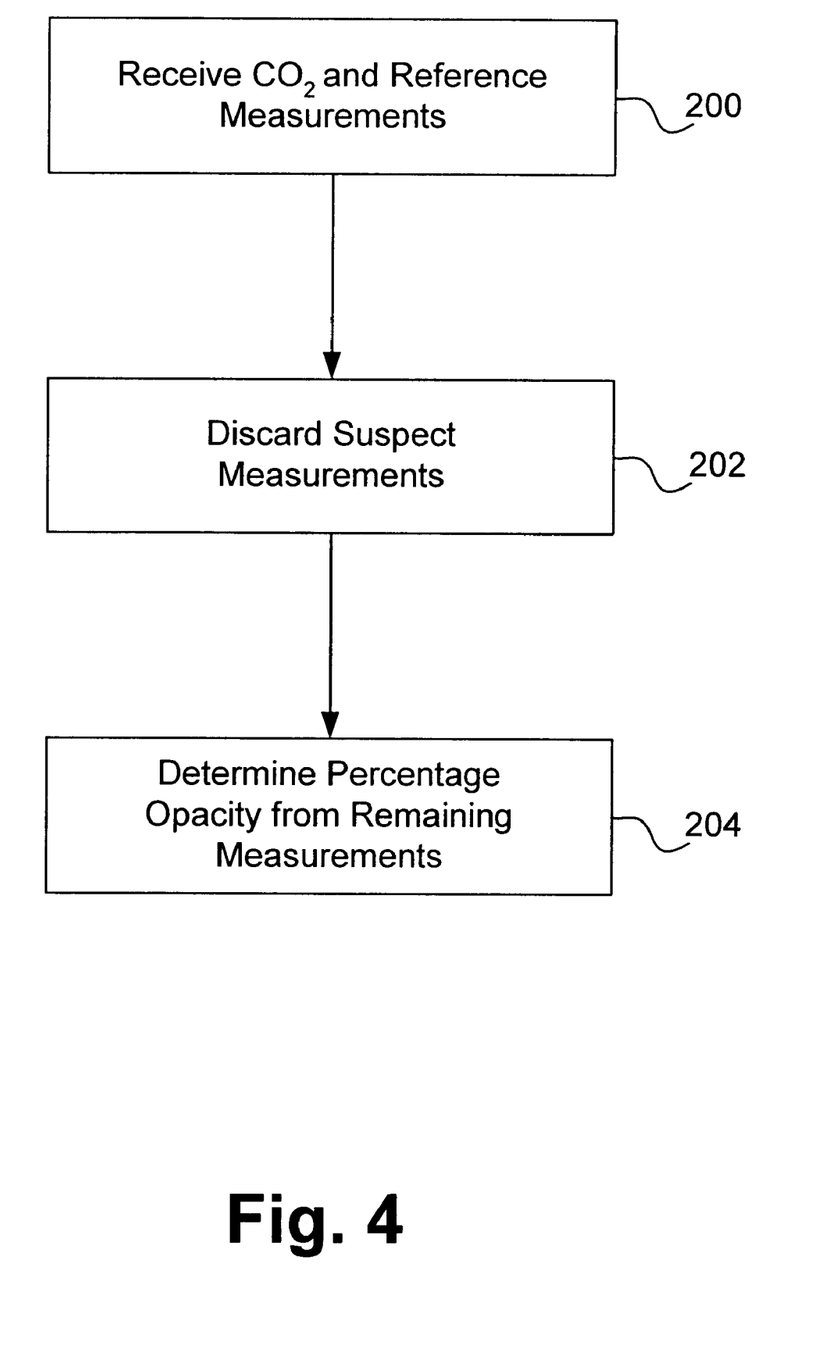
FIG. 4 depicts a flow diagram of a method according to one embodiment of the present invention.

FIG. 4 depicts a flow diagram of a method for detecting exhaust opacity according to an embodiment of the present invention. In step 200, the output of a reference channel and one or more emission channels, for example, the $CO_2$ channel, may be received by processor 100. Various validation, error prevention or signal processing routines may be performed on the data to ensure that the plume is sufficient for making an opacity determination. In step 202, if these validation routines determine that the plume is insufficient then the plume may be labeled as suspect or discarded to prevent erroneous opacity measurements.

If, however, the measurements are validated, then in step 204, processor 100 may determine percentage opacity from the remaining measurements. Specifically, percentage opacity may be determined by calculating the slope of the reference channel output versus the slope of the $CO_2$ channel output. In addition, these results may be converted to provide a Ringelman scale equivalent. Simply stated, a Ringelman scale equivalent is determined by equating percentage opacity to a number between 0 and 5. The Ringelman scale, which is a standard opacity scale used by suitably trained observers, may be compared to the opacity may be as follows:

| Opacity | Ringelman Equivalent |
| --- | --- |
| 0% | 0 |
| 15% | 1 |
| 30% | 2 |
| 50% | 3 |
| 70% | 4 |
| 100% | 5 |

After the percentage opacity is determined, it may be desired to validate the opacity measurements through one or more validation routines. Specifically, according to one embodiment, all percentage opacities below a predetermined amount should be labeled as suspect. In one embodiment, the predetermined amount may be −5.0%, although other values may also be used.

Additionally, in determining the reference slope using least squares, a slope error value may also be determined according to known methods. Based on that slope error, an opacity error value is determined by multiplying this value by a predetermined value. According to one embodiment, the predetermined factor may be 1000, for example. According to another embodiment of the present invention, the factor may be 100. If this opacity error value exceeds a predetermined value, then the percentage opacity measurement is labeled as suspect. The predetermined value for the opacity error may be 2%, for example.

Also, percentage opacity measurements above a certain level of opacity may be labeled as suspect or discarded. For example, it may be determined that a measurement of greater than about 50% opacity should be discarded because it is likely that such a high amount of opacity would not be readable accurately and instead may indicate light blockage or another type of temporary problem that does not reflect opacity of the exhaust stream. Other predetermined values, such as 70%, 80%, 90% or 100%, for example, may also be used.

In the case of diesel powered vehicles, the most preferred validation method is to compare the opacity measurement to a measurement of CO taken at the same time since there is a correlation between CO emissions and exhaust opacity for diesel vehicles. Using this method, predetermined correlations between CO and opacity measurements can be used to determine whether a particular opacity measurement should be considered valid, suspect or invalid.

Accordingly, a device according to the present invention may remotely determine opacity over a brief time interval from a moving vehicle. Further, because many existing emission monitoring devices utilize a reference channel for other purposes, a device according to the present invention may be utilized with existing systems to provide opacity measurements. According to one embodiment, use of processor 100 with existing systems permits an existing emission monitoring system to monitor opacity as well. Therefore, replacement costs may be minimized.

Multiple Wavelength Opacity Measurement

Figure 5:
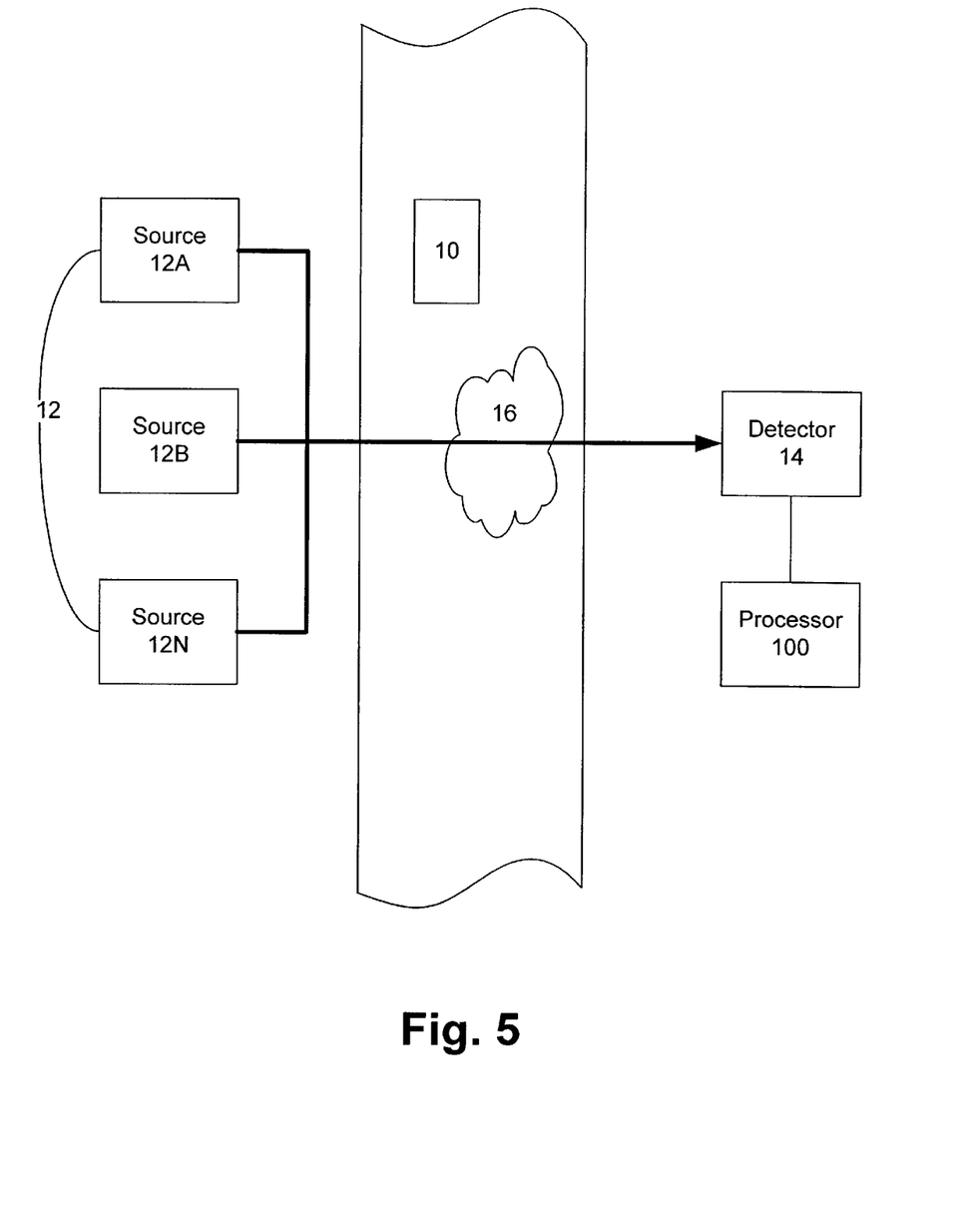
FIG. 5 is a schematic view of a multiple wavelength opacity measurement system according to some embodiments of the invention.

FIG. 5 is a schematic of a multi-wavelength opacity measuring system according to one embodiment of the invention. The system may comprise a source 12 capable of producing multiple wavelengths of EM radiation. For example, source 12 may comprise a number of sources (e.g., source 12A, source 12B, . . . , source 12N) that produce EM radiation in differentiable regions of the EM spectrum. For example, in a three wavelength embodiment of the invention, source 12 may comprise a an infrared (IR) source (e.g., a silicon carbide electrically heated igniter, a tunable diode laser, etc.), a visible source (e.g., a He-Ne laser) and a ultraviolet (UV) source (e.g., a xenon, mercury, deuterium, or other arc lamp).

While source 12 is shown as comprising separate sources (e.g., source 12A, source 12B, . . . , source 12N) in FIG. 5, the invention is not so limited. A single source capable of producing EM radiation in differentiable wavelengths (e.g., a tunable laser source or the like), a combination of tunable and discrete wavelength sources, or some other scheme for producing differentiable wavelength EM radiation may be used.

Source 12 produces EM radiation 20 that is directed through an emission source (e.g., exhaust plume 16). Radiation 20 may be directed through the emission source in any suitable manner. For example, radiation 20 may be directed directly through an emission source using appropriate optics (e.g., lenses, mirrors, beam splitters, polarizers, filters, retro-reflectors and other optics).

As schematically indicated in FIG. 5, the emitted radiation from multiple sources (e.g., source 12A, source 12B, . . . , source 12N) may be combined into a single beam, however, the invention is not so limited. Multiple beams may be directed through the emission source (e.g., exhaust plume 16) or other beam geometries may be employed, for example, some of the beams may originate from locations that are different than the location of other beams (e.g., beams may originate from sources located on opposite sides of the emissions source). For example, in one embodiment the IR and UV sources may be located on one side of the emissions source and the visible source may be located on another side of the emissions source. In such an embodiment the IR and UV radiation complete a single pass through the exhaust plume 16 and the visible radiation executes a double pass through the exhaust plume. Retro-reflectors or other beam direction devices (e.g., lenses, mirrors, beam splitters, etc.) may be used to direct the beams.

In embodiments of the invention that also detect concentrations of exhaust plume 16 constituents, one or more of source 12A, . . . , source 12N may be tuned to wavelengths appropriate absorption wavelengths. Other arrangements may also be used. For example, separate sources 12 may be provided for absorption measurements and for opacity measurements or the same source 12 may be alternately tuned to absorption and opacity measurement wavelengths.

While passing through the emission source (e.g., exhaust plume 16), portions of the incident radiation 20 may be absorbed, scattered or otherwise attenuated by constituent particles in the emission source. After exiting the emission source, post plume radiation 22 is directed into an appropriate detector 14. For example, in a three beam embodiment the UV radiation may be detected using a monochromator and diode array (e.g., a silicon diode array), the visible radiation may be detected with a photo-multiplier tube (PMT) (and filters, if necessary) and the IR radiation may be detected by appropriate IR detectors (e.g., photo-diodes or the like). Other detectors may also be used (e.g., charge coupled devices (CCD), or other radiation detectors).

FIG. 5 indicates a single pass geometry for the source-detector combination (i.e., radiation 20 makes a single pass through the emission source before reaching detector 14), however, the invention is not so limited. For example, source 12 and detector 14 may be positioned on the same side of an emission source and appropriate optics (e.g., mirrors, lenses, or other beam directors) may be used to direct post exhaust plume radiation 22 to detector 14. Other geometries are also possible.

Signals from detector 14 may be input into processor 100. Processor 100 may comprise any suitable processing device. For example, a personal computer, lap-top or notebook computer, a hand held processor, a stand-alone processing device, or any other device capable of performing the processing functions described herein.

Figure 6:
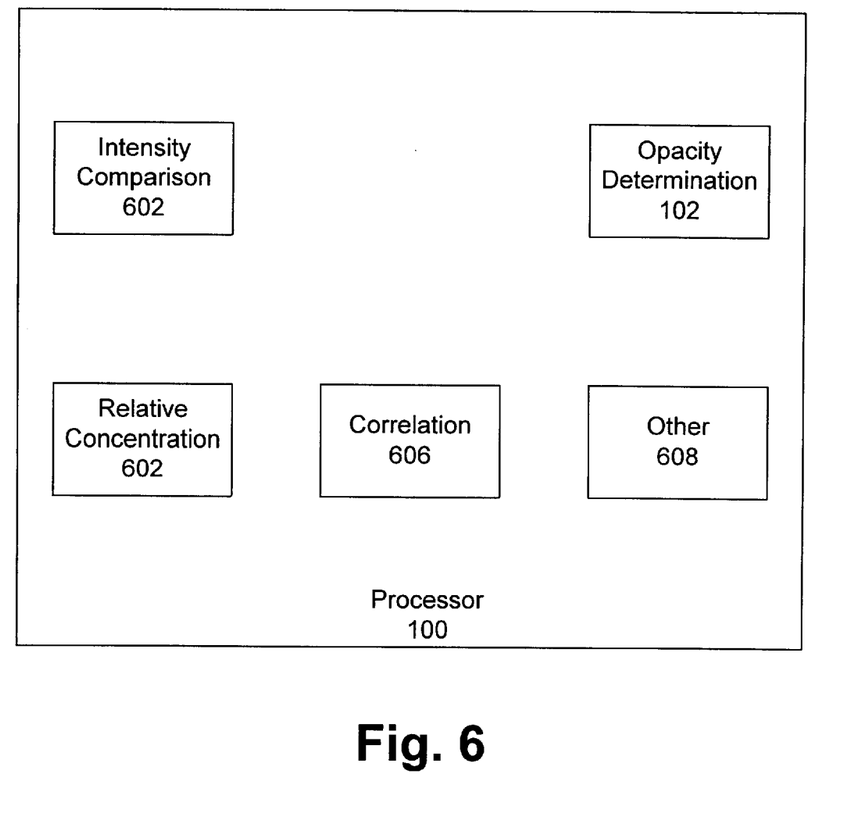
FIG. 6 is a schematic view of a processor according to some embodiments of the invention.

As shown schematically in FIGS. 1, 3 and 6 processor 100 may comprise a number of modules for executing processing functions. For example, processor 100 may comprise an opacity determination module 102, an intensity comparison module 602, a relative concentration module 604, a correlation module 606, and processing modules 608. While processor 100 is shown having numerous separate modules, the invention is not so limited. Modules (e.g., 102, 602, etc.) may comprise sub-routines of a single software package, individual software packages, or some other combination of software modules that enable processor 100 to perform the functions described herein.

Figure 7:
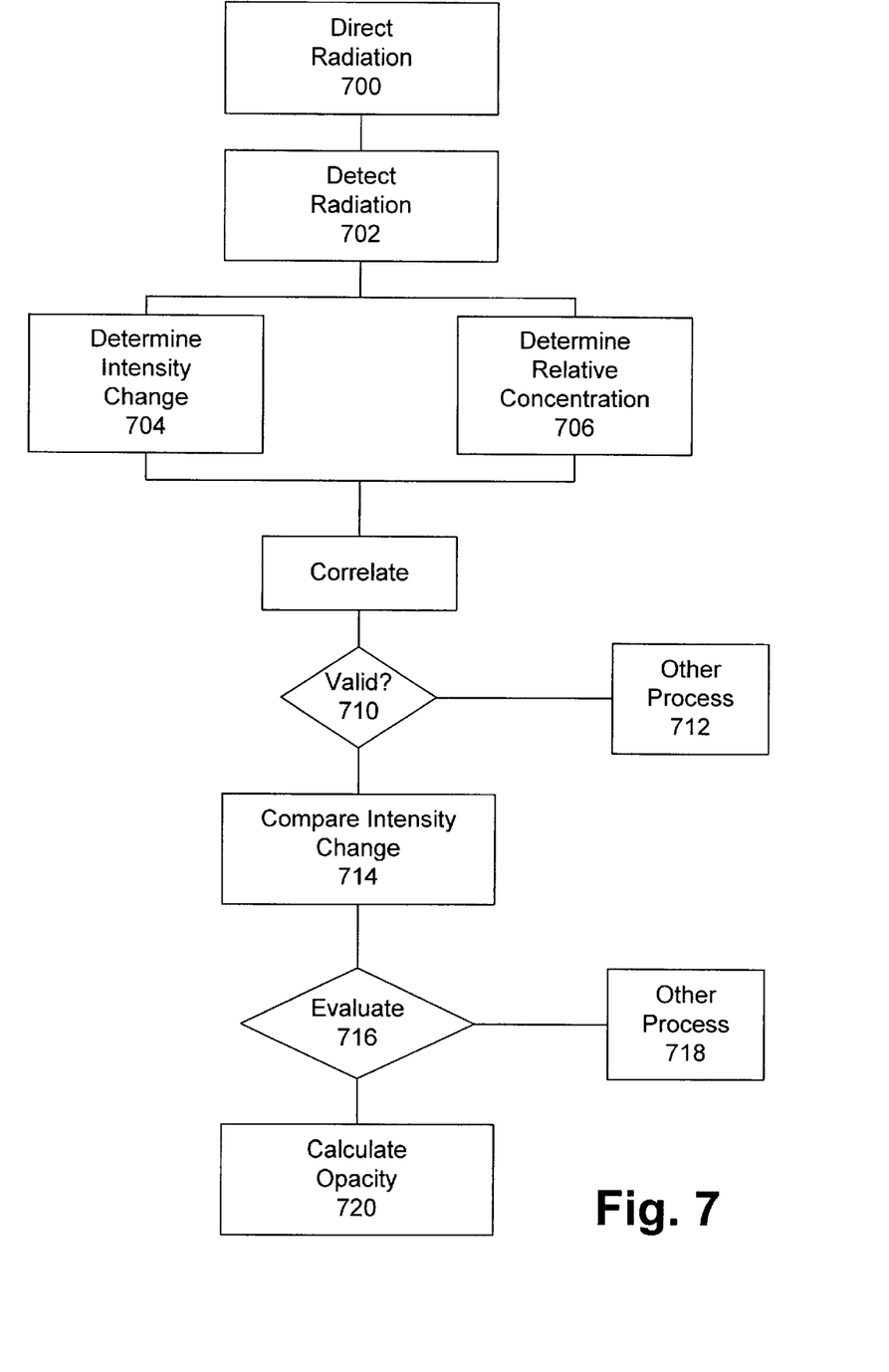
FIG. 7 is a flow diagram illustrating a method for determining an opacity value according to some embodiments of the invention.

The operation of the opacity detection system may be described with reference to FIG. 7. FIG. 7 shows a method for determining opacity of an emission source according to one embodiment of the invention. EM radiation of differing wavelengths is directed through an exhaust plume as indicated at 700. As described above, the radiation may be directed using appropriate beam directors and may comprise one or more beams of EM radiation. As also described above, at least some of the EM radiation wavelengths are conveniently chosen to correspond to wavelengths for which absorption and/or scattering due to "smoke" particles will occur (e.g. 0.8–4 $\mu$m for IR, 400–800 nm for visible and 200–223 and 233–400 nm for UV). These are referred to collectively as "opacity wavelengths." In addition, one or more of the EM wavelengths may be conveniently chosen to correspond to absorption wavelengths for one or more emission source constituents (e.g. CO, $CO_2$, NO, $NO_x$, HC, $H_2O$, etc.).

The EM radiation is detected as indicated at 702. As discussed above, the EM radiation may be detected in any appropriate manner and after the EM radiation has performed any number of passes through the emissions source. Signals from the detector (e.g., detector 14) are communicated to a processor (e.g., processor 100).

Processing of the information in the detector signals occurs next. Processing may occur in different orderings than shown in FIG. 7. This is indicated schematically by the adjacent placing of items 704 and 706 in FIG. 7.

Processor 100 determines the change in intensity for the opacity wavelengths as indicated at 704. Processor 100 may accomplish the change in intensity determination in any suitable fashion. For example, an intensity comparison module (e.g., module 602) may be used. In some embodiments, the change in intensity is a comparison of the intensity of the beam signal as measured at detector 14 with the beam not intercepting the exhaust plume 16 and the intensity of the beam signal as measured with the beam passing through the exhaust plume 16. Such a measurement may be implemented by any suitable scheme as discussed above (e.g., pre-block signal indicates state before vehicle passage and post-block signal indicates state after vehicle has passed).

Processor 100 may also determine the relative concentration of one or more exhaust plume constituents (e.g., CO, $CO_2$, NO, $NO_x$, HC, $H_2O$, etc.) as indicated at 706. The relative concentrations may be obtained as described above, or in any other suitable manner.

The relative concentration values may be used for correlation with the opacity measurements. Any concentration value may be used for correlation, however, using the sum of CO and $CO_2$ concentration values may be advantageous. For example, if the result of a $CO_2$ concentration measurement is a valid $CO_2$ value, and if the result of a CO concentration measurement is a valid CO value, then the correlation of absorption at the opacity wavelengths to the observed CO, $CO_2$ sum is a measure of the fuel specific opacity (i.e., smoke per gallon of fuel). Alternatively, correlation may be against total carbon in the emission source which, for most hydrocarbon fuels, is equivalent to $CO_2$+CO+6HC. In most cases the $CO_2$ term dominates and may be used by itself as a first approximation correlation value.

Correlation of the opacity wavelength measurement is performed as indicated at 708. Correlation may be performed in any suitable manner. For example, the changes in intensity for the opacity wavelengths (e.g. obtained at 704) may be compared to the changes in $CO_2$ measurements made during the same time interval.

The degree of correlation may be evaluated in any suitable fashion. For example, the correlation may be compared with predetermined criteria (e.g., a regression line with a standard error of the slope less than 20% of the slope value) to determine whether the opacity wavelength measurement is valid. This is indicated at 710.

If the evaluation at 710 indicates that the opacity wavelength measurement is not valid, then the data may be passed to other processing routines as indicated at 712. Other processing may include flagging or otherwise marking the data as suspect or invalid, discarding the data, or other appropriate processing.

If the evaluation at 710 indicates that the opacity wavelength measurement is valid, then the process continues as indicated at 714. At 714, a predetermined number of the multiple opacity wavelength measurements are compared. Any number of opacity wavelength measurements may be compared. For example, in a three wavelength embodiment, the opacity wavelength measurements for IR, UV and visible wavelengths may be compared.

The opacity wavelength measurements may be compared to evaluate any suitable criteria. For example, the change in intensity (e.g., with and without passing through the emissions source) for a predetermined number of the opacity wavelength beams may be compared.

At 716 an evaluation of the comparison at 714 may occur. Any appropriate evaluation may be used. For example, an evaluation of the degree of equivalence for a predetermined number of the intensity change measurements may be performed.

If the result of the evaluation at 714 is that the comparison is not valid (e.g., the measurements do not agree within the predetermined degree of equivalence), then the data may be passed for other processing as indicated at 718. Processing at 718 may comprise any suitable processing routines (e.g., flagging, discarding, etc.).

If the result of the evaluation at 714 is that the comparisons are valid (e.g., the measurements agree within a predetermined degree of equivalence), then the process may continue to a calculation of an opacity value for the emissions source. This is indicated at 720.

Calculation of an opacity value for the emissions source may be accomplished in any suitable manner. For example, valid change in intensity measurements (e.g., as determined at 704 and validated at 710 and 716) may be averaged to report an opacity value for the emissions source. Weighted averages or other manipulations of the data may also be performed to calculate an opacity value.

Monochromatic Opacity Measurement

Small non-absorbing particles (i.e., smoke) in a beam of EM radiation reduce the transmitted energy in the beam. The amount of reduction in monochromatic EM beam is typically defined by Beer's Law as:

$$T = e^{-k_s n_s}.$$

Where T is the transmittance of the light at a specified wavelength, $n_s$ is the amount of smoke per unit cross-section of the light beam, and $k_s$ is the extinction coefficient that applies for specified wavelength of EM radiation and for a given particle size. The units of $k_s$ are the inverse of $n_s$.

As discussed above, determining the amount of $CO_2$ in a vehicle exhaust plume 16 is known. As also discussed above, the $CO_2$ from the exhaust is a direct result of combustion processes taking place within the vehicle. The amount of $CO_2$ produced in the exhaust is generally proportional to the amount of fuel involved in the combustion process.

Smoke formulation in an exhaust plume is also generally the result of combustion processes. Therefore, for a given engine operating condition it is reasonable to assume that the amount of smoke produced is also proportional to the amount of $CO_2$ produced. That is:

$$n_s = k n_{CO_2}.$$

Where $n_s$ is the amount of smoke, k is a constant of proportionality, and $n_{CO2}$ is the amount of $CO_2$.

The above generally applies to the entire emission plume or to a portion of the plume provided all measurements refer to the same portion. Therefore, Beer's Law can be restated as:

$$T = e^{-k_s n_s} = e^{-k_s k n_{CO2}} = e^{-K_s n_{CO2}}.$$

Where $K_s$ is product of $k_s$ and k.

The above implies that by simultaneously measuring the amount of $CO_2$ ($n_{CO2}$) with one beam of EM radiation, and by then measuring the transmittance (T) with another beam of EM radiation through the same spatial volume, the opacity value, $K_s$, can be computed as:

$$K_s = \frac{\ln\left(\frac{1}{T}\right)}{n_{co_2}}.$$

Where T is the measure transmittance (T) of a monochromatic EM radiation of wavelength that is short enough to sense the smoke particles and also is a wavelength that is not subject to absorption of typical gases of automotive exhaust (e.g., 0.8–4 μm, 400–800 nm, 200–223 nm, 233–400 nm, etc.). From the measurement of $K_s$ and literature values for $k_s$ it is straightforward to determine particle mass emissions per kilogram or per gallon of fuel.

Figure 8:
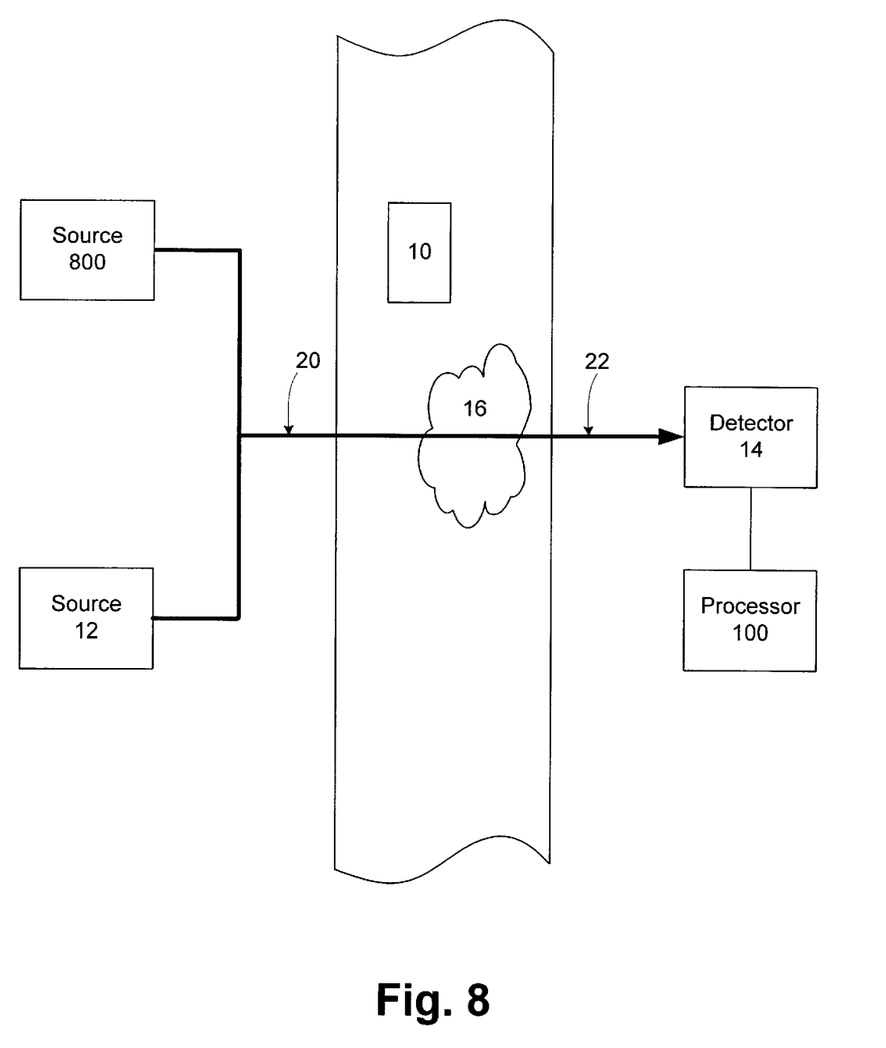
FIG. 8 is a schematic diagram illustrating a monochromatic opacity measurement system according to some embodiments of the invention.

One embodiment of a monochromatic opacity measurement system may comprise a remote emissions sensing system (RES) enabled to detect vehicle exhaust emissions and, in addition, measure and compensate for smoke particles in the exhaust. This is shown in FIG. 8. For example, the RES may comprise a source 12 to emit EM radiation that enables detection of the exhaust constituents and monochromatic (i.e., single, or nearly single wavelength) EM radiation source 800 that enables detection of the opacity of exhaust plume 16. The combined source 12, 800 may comprise multiple sources that emit EM radiation of differing wavelengths, a single source that is capable of tuning over multiple wavelengths or some other combination of EM transmission sources.

Figure 9:
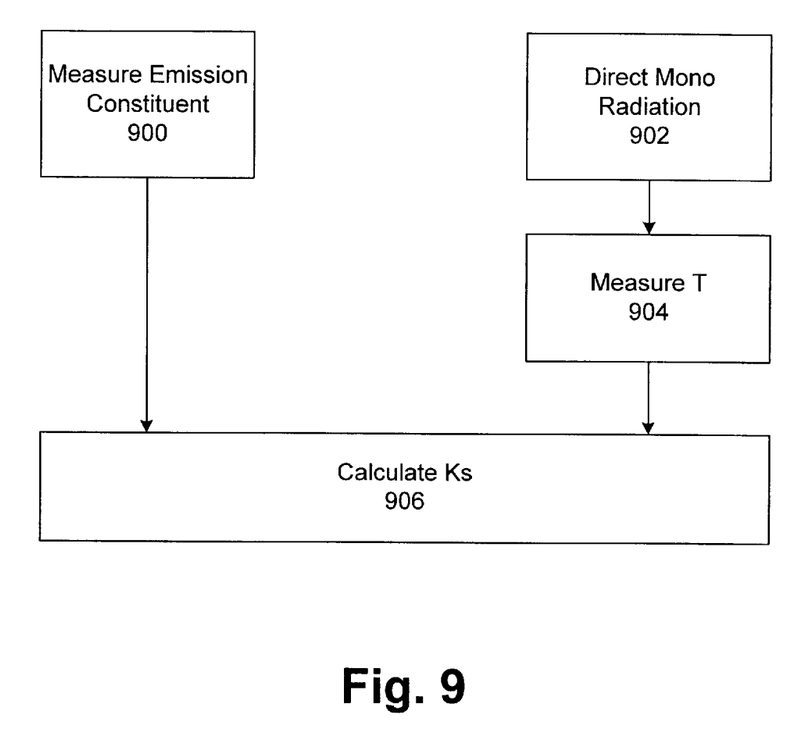
FIG. 9 is a schematic flow diagram illustrating a method for determining an opacity value according to some embodiments of the invention.

FIG. 9 is a flow diagram illustrating a method for calculating an opacity value $K_s$. An amount for an emission source constituent is measured at 900. The measurement may take place at any suitable time (e.g., slightly before, slightly after, or simultaneously with the transmission of monochromatic EM radiation through the emission source). Measurement 900 may also be for any suitable emission source constituent (e.g., NO, $NO_x$, CO, $CO_2$, $H_2O$, HC, etc.), however, as discussed above, it may be advantageous to measure the amount of $CO_2$.

Monochromatic EM radiation is directed through the emission source as indicated at 902. As indicated above, this may occur at any suitable time (before, after, or simultaneous). Care should be taken, however, to insure that the monochromatic EM radiation and measurement 900 are taken for substantially the same volume of emission source. For example, a measurement of substantially the same emission source volume may be accomplished by using a fractional second delay between beam transmission (e.g., 0–5 ms), or by directing a combined beam through the emission source volume.

A measurement of monochromatic EM radiation transmittance is performed at 904. Transmittance may be measured in any suitable manner (e.g., with detector 14 as described above).

A calculation of the opacity value $K_s$ may be performed at 906. Calculation may be performed in any suitable fashion. For example, processor 100 may be used to calculate an opacity value according to the relation $$K_s = \frac{\ln\left(\frac{1}{T}\right)}{n_{co_2}}.$$

In some embodiments, an opacity measurement may be carried out at wavelengths that are comparable on average to the mass mean diameter, of non-absorbing smoke particles. For example wavelengths in the ultraviolet (UV) portion of the EM spectrum may be used (e.g., 200–400 nm, not including 224–232 nm).

In addition, the wavelengths of EM radiation that are selected to opacity may be selected from portions of the UV spectrum for which absorption by exhaust constituents (e.g., CO, $CO_2$, NO, $NO_x$, HC, etc.) is substantially negligible. This enables the transmittance measurement to be relatively unaffected by absorption by exhaust constituents.

In addition, the wavelengths used to measure opacity may be substantially monochromatic or of a relatively narrow bandwidth. By maintaining relatively narrow bandwidth EM radiation the calculations derived from Beer's Law apply more accurately and yield good experimental agreement (e.g., an approximately linear correlation between $K_s$ and $n_{CO2}$). For example, a laser or spectrometer may be used to provide relatively monochromatic measured EM radiation. Other sources may be used.

The detectors used to detect the EM radiation may also be selected according to the types of EM radiation sources used. For example, if UV radiation is emitted from a source, then UV detectors may be used. In some embodiments a UV spectrometer may be used to detect the source-emitted EM radiation. Other detectors may be used.

In one embodiment of the invention, the measurement of opacity in exhaust emissions may be accomplished according to the following scheme. An EM source 12, 800 directs a beam of EM radiation (e.g., 20) through an exhaust emission plume 16. For example, a combined beam of infrared (IR) and UV radiation may be directed through the exhaust plume of a vehicle. The IR component of the beam may be used to measure the amount of $CO_2$ and other exhaust constituents in a known manner. The UV component of the beam may be used to measure the transmittance of the beam through the same portion (i.e., spatial volume) of the exhaust plume. The measurements for the transmittance (T) and the amount of exhaust constituents (e.g., $n_{CO2}$) may be used to compute a smoke density value ($K_s$) as indicated above, using:

$$K_s = \frac{\ln\left(\frac{1}{T}\right)}{n_{co_2}}.$$

Other schemes may be used to record measurements of the exhaust constituents (e.g., $CO_2$) and opacity. For example, a first beam of EM radiation (e.g., one from source 12) may be directed through a portion of an exhaust plume at a first time and a second beam of EM radiation (e.g., one from source 800) may be directed through the exhaust plume 16 slightly later (e.g., a fraction of a millisecond) in order to record the amount of exhaust constituent and transmittance.

In some embodiments, the opacity value ($K_s$) may be used as a correction factor to other exhaust emission measurements. For example, $K_s$ may be used, in some cases, with a wavelength dependent scaling factor to correct measurements of the relative amounts of exhaust constituent concentration (e.g., the amounts of CO, NO, $NO_x$, HC, etc.).

In addition, the opacity value $K_s$ may be used as a separate measurement value that may be used in exhaust emission monitoring. For example, the value of $K_s$ may be recorded and compared to predetermined values indicative of proper vehicle operating conditions. For example, recorded values of $K_s$ outside of the predetermined range may result in a "failure" of the vehicle being monitored in the emission test. Other uses for the opacity value are also possible.

Other embodiments and uses of the invention will be apparent to those skilled in the art from consideration of the specification and practice of the invention disclosed herein. The specification and examples should be considered exemplary only. The scope of the invention is only limited by the claims appended hereto.

What is claimed is:

1. A method for determining an opacity value of an emission plume the method comprising the steps of:

directing a beam comprising at least two different wavelengths of electromagnetic radiation through an emission plume;

detecting the beam after the beam has passed through the emission plume;

determining a change in intensity of the beam for each of the at least two different wavelengths of electromagnetic radiation;

comparing the change in intensity for a predetermined number of measurements of the at least two different wavelengths of electromagnetic radiation, and, if the change in intensity for the predetermined number of measurements of the at least two different wavelengths of electromagnetic radiation is substantially equivalent, determining an opacity value related to the change in intensity for the predetermined number of measurements of the at least two different wavelengths of electromagnetic radiation.

2. The method of claim 1, wherein the beam further comprises:

a first wavelength that is substantially in the infrared spectrum;

a second wavelength that is substantially in the visible spectrum; and a third wavelength that is substantially in the ultra-violet spectrum.

3. A method for measuring opacity using a remote emission sensing system that measures on-road vehicle exhaust emissions, the method comprising:

directing at least two different wavelengths of electromagnetic radiation through an exhaust emission plume;

detecting the at least two wavelengths of electromagnetic radiation after they pass through the exhaust emission plume;

determining the relative concentration of a vehicle exhaust constituent present in the exhaust emission plume;

determining a change in intensity for each of the at least two different wavelengths of electromagnetic radiation;

correlating the change in intensity for each of the at least two different wavelengths of electromagnetic radiation to the determined relative concentration of the vehicle exhaust constituent;

registering a valid opacity value for each of the at least two different wavelengths of electromagnetic radiation that substantially correlate to the determined relative concentration of the vehicle exhaust constituent;

comparing the change in intensity for a predetermined number of the at least two different wavelengths of electromagnetic radiation and, if the change in intensity for the predetermined number of the at least two different wavelengths of electromagnetic radiation is substantially equivalent, calculating a reported opacity value proportional to an average of the valid opacity values.

4. The method of claim 3, further comprising:

directing a third different wavelength of electromagnetic radiation through the exhaust emission plume.

5. The method of claim 4 wherein, a first of the at least two different wavelengths of electromagnetic radiation comprises a wavelength that is substantially in the infrared spectrum;

a second of the at least two different wavelengths of electromagnetic radiation comprises a wavelength that is substantially in the visible spectrum; and the third different wavelength of electromagnetic radiation comprises a wavelength that is substantially in the ultra-violet spectrum.

6. A remote sensing system for measuring opacity of a vehicle exhaust plume the system comprising:

a source that directs at least two different wavelengths of electromagnetic radiation through an exhaust emission plume;

a detector that detects the at least two different wavelengths of electromagnetic radiation and produces an output signal; and a processor comprising:

a relative concentration module that determines a relative concentration of a vehicle exhaust constituent present in the exhaust emission plume;

a change in intensity module that determines a change in intensity for the at least two different wavelengths based, at least in part, upon the output signal;

a correlation module that correlates the change in intensity for the at least two different wavelengths to the relative concentration of the vehicle exhaust constituent and registers a valid opacity value for each of the at least two different wavelengths that substantially correlate to the determined relative concentration of the vehicle exhaust constituent; and     a calculation module that compares the change in intensity for a predetermined number of the at least two different wavelengths of electromagnetic radiation and, if the change in intensity for the predetermined number of the at least two different wavelengths is substantially equivalent, calculates a reported opacity value proportional to the average of the valid opacity values.

7. The system of claim 6 further comprising:

a source of electromagnetic radiation comprising a third different wavelength.

8. The system of claim 7 wherein, a first of the at least two different wavelengths of electromagnetic radiation comprises a wavelength that is substantially in the infrared spectrum;

a second of the at least two different wavelengths of electromagnetic radiation comprises a wavelength that is substantially in the visible spectrum; and the third different wavelength comprises a wavelength that is substantially in the ultra-violet spectrum.

\* \* \* \* \*